(12) United States Patent
Bukhamseen et al.

(10) Patent No.: US 10,890,067 B2
(45) Date of Patent: Jan. 12, 2021

(54) METHOD TO USE A BUOYANT BODY TO MEASURE TWO-PHASE FLOW IN HORIZONTAL WELLS

(71) Applicant: Saudi Arabian Oil Company, Dhahran (SA)

(72) Inventors: Ahmed Bukhamseen, Dammam (SA); Brett W. Bouldin, Dhahran (SA); Rob Turner, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 98 days.

(21) Appl. No.: 16/381,777

(22) Filed: Apr. 11, 2019

(65) Prior Publication Data
US 2020/0325772 A1 Oct. 15, 2020

(51) Int. Cl.
*E21B 49/08* (2006.01)
*E21B 47/06* (2012.01)
(Continued)

(52) U.S. Cl.
CPC .............. *E21B 49/08* (2013.01); *E21B 34/08* (2013.01); *E21B 43/12* (2013.01); *E21B 47/06* (2013.01);
(Continued)

(58) Field of Classification Search
CPC .......... E21B 43/12; E21B 43/08; E21B 43/34; E21B 47/10; E21B 47/06; E21B 49/08;
(Continued)

(56) References Cited

U.S. PATENT DOCUMENTS

| 5,348,041 A | 9/1994 | Clark |
| 5,741,977 A | 4/1998 | Agar et al. |

(Continued)

FOREIGN PATENT DOCUMENTS

| EP | 2708858 A1 | 3/2014 |
| WO | 0122041 A1 | 3/2001 |

(Continued)

OTHER PUBLICATIONS

International Search Report and Written Opinion for International Application No. PCT/US2020/027515 dated Jun. 29, 2020; pp. 1-18.

*Primary Examiner* — Peter J Macchiarolo
*Assistant Examiner* — David L Singer
(74) *Attorney, Agent, or Firm* — Bracewell LLP; Constance G. Rhebergen; Brian H. Tompkins

(57) ABSTRACT

A method for the determination of the water cut and volumetric flow rate of a fluid flowing through a density inflow control valve. A density inflow control valve may include a floating device that moves between a relaxed choke position and a restricted choke position depending on the density of the fluid flowing through the valve. Pressure gauges upstream and downstream of the inflow control device may be used to measure the pressure drop across the inflow control valve over time. The water cut of the downhole fluid flowing through the valve may be determined from the pressure drop over time and the pressure drop associated with the relaxed choke position and the restricted choke position. The volumetric flow rate may be determined from the average water cut and the density of the downhole fluid, as determined from the single phase densities.

25 Claims, 4 Drawing Sheets

(51) Int. Cl.
  *E21B 47/10* (2012.01)
  *G01N 33/28* (2006.01)
  *G01N 11/08* (2006.01)
  *E21B 43/12* (2006.01)
  *E21B 34/08* (2006.01)
  *G01F 1/40* (2006.01)
  *G01F 1/74* (2006.01)
  *G01F 1/88* (2006.01)

(52) U.S. Cl.
  CPC ............ *E21B 47/10* (2013.01); *G01F 1/40* (2013.01); *G01F 1/74* (2013.01); *G01F 1/88* (2013.01); *G01N 11/08* (2013.01); *G01N 33/2823* (2013.01); *G01N 33/2847* (2013.01); *E21B 49/0875* (2020.05)

(58) Field of Classification Search
  CPC ......... E21B 49/0875; G01F 1/74; G01F 1/88; G01F 1/40; G01F 1/42; G01N 11/08; G01N 33/2823; G01N 33/2847; G01N 33/1833; G01N 9/26; G01N 11/04; B01D 17/0214; Y10T 137/3006; Y10T 137/87322; Y10T 137/87499; F16K 31/18; F16K 31/22; F16K 31/30; F16K 33/00
  USPC ....................................... 73/61.78
  See application file for complete search history.

(56) References Cited

U.S. PATENT DOCUMENTS

| | | | |
|---|---|---|---|
| 6,831,470 B2 | 12/2004 | Xie et al. | |
| 6,860,325 B2 | 3/2005 | Ramakrishnan et al. | |
| 6,993,979 B2 | 2/2006 | Segeral | |
| 7,908,930 B2 | 3/2011 | Xie et al. | |
| 8,561,842 B2 | 10/2013 | Pizzacalla et al. | |
| 9,116,105 B2 | 8/2015 | Veneruso et al. | |
| 2003/0062324 A1 | 4/2003 | Abrams et al. | |
| 2004/0144544 A1* | 7/2004 | Freyer | E21B 43/08 166/369 |
| 2006/0076150 A1* | 4/2006 | Coronado | E21B 34/10 166/386 |
| 2006/0113089 A1* | 6/2006 | Henriksen | E21B 34/08 166/386 |
| 2008/0035350 A1* | 2/2008 | Henriksen | E21B 34/08 166/313 |
| 2008/0041581 A1* | 2/2008 | Richards | E21B 34/08 166/193 |
| 2008/0041582 A1* | 2/2008 | Saetre | E21B 34/08 166/205 |
| 2008/0060846 A1* | 3/2008 | Belcher | E21B 43/08 175/25 |
| 2008/0283238 A1 | 11/2008 | Richards et al. | |
| 2009/0101344 A1* | 4/2009 | Crow | E21B 43/12 166/285 |
| 2009/0101353 A1* | 4/2009 | Crow | E21B 43/12 166/373 |
| 2009/0151925 A1* | 6/2009 | Richards | E21B 34/06 166/53 |
| 2010/0230347 A1 | 9/2010 | Haslem | |
| 2013/0068467 A1* | 3/2013 | Zhou | E21B 43/12 166/369 |
| 2014/0034308 A1 | 2/2014 | Holderman et al. | |
| 2014/0136125 A1 | 5/2014 | Agar et al. | |
| 2015/0083402 A1 | 3/2015 | Manin | |
| 2019/0120048 A1* | 4/2019 | Coffin | E21B 43/12 |

FOREIGN PATENT DOCUMENTS

| | | | |
|---|---|---|---|
| WO | 2013005091 A2 | 1/2013 | |
| WO | 2014123539 A1 | 8/2014 | |
| WO | 2015199545 A1 | 12/2015 | |
| WO | 2018063149 A1 | 4/2018 | |
| WO | WO-2019112597 A1 * | 6/2019 | ............ E21B 43/38 |
| WO | WO-2019160423 A1 * | 8/2019 | ............ E21B 43/12 |

* cited by examiner

METHOD TO USE A BUOYANT BODY TO MEASURE TWO-PHASE FLOW IN HORIZONTAL WELLS

BACKGROUND

Field of the Disclosure

The present disclosure generally relates to the measurement of fluids in wells used to access hydrocarbon reservoirs. More specifically, embodiments of the disclosure relate to the measurement of the water cut and flow rate of fluids in horizontal wells.

Description of the Related Art

Wells may be drilled into rocks to access fluids stored in geographic formations having hydrocarbons. Such a geographic formation may contain or be referred to as a "reservoir." Information about fluids in a hydrocarbon reservoir is important for properly characterizing the reservoir and conducting optimal drilling and production operations to efficiently extract hydrocarbons. Certain types of wells, such as horizontal wells, may present particular challenges in obtaining such information and monitoring the well. Existing techniques have particular limitations, may be expensive, and may require time-consuming intervention operations. Moreover, the determination and inaccuracy of existing techniques may result in delays or inefficiencies in production from the well.

SUMMARY

Some horizontal wells may be completed with an inflow control device (ICD) to assist in optimizing production. The monitoring of horizontal wells completed with an inflow control device is typically performed using production logging tools that have a relatively high cost of operation compared to other tools and may require extensive coiled tubing operation. In some instances, multiphase flow meters may be used to monitor horizontal wells. Such multiphase flow meters may use several sensors and algorithms to interpret complex flows, such as mixtures of oil, water, and gas and, in some cases, solids. A typical sensor arrangement for such multiphase flow meters may include a Venturi meter to measure mass flow rate and a nuclear source and associated detector to measure density. However, the use of nuclear sources in downhole applications may be undesirable. Alternative sensor technologies, like x-rays or microwaves, are generally not sufficiently reliable for long-term use in downhole environments having relatively great temperatures as compared to other downhole environments.

Embodiments of the disclosure generally relate to the determination of the water cut and volumetric flow rate of a downhole fluid flowing through an inflow control device. Water cut refers to the ratio of water to the volume of total fluids and may be expressed as a percentage or decimal value. The water cut value and volumetric flow rate determined using the techniques described in the disclosure may be significantly faster than existing techniques and may decrease costs. For example, the techniques described in the disclosure avoid the use of well intervention or production logging operations that are relatively expensive, time-consuming, and intrusive. Additionally, the techniques described in the disclosure eliminate the use of nuclear sources and x-ray or microwave devices for measuring downhole fluids, as such sources and devices may present safety and reliability problems.

In one embodiment, a method of determining properties of a downhole fluid in a well is provided. The method includes using a pressure drop device in the well, in combination with a moveable device configured to move between a first position and a second position. The first position is associated with a first water cut for a downhole fluid and the second position is associated with a second water cut for the downhole fluid, such that the first water cut is greater than the second water cut. The method also includes determining a first pressure drop across the pressure drop device associated with the first position and determining a second pressure drop across the pressure drop device associated with the second position. The method further includes determining an instantaneous water cut value in a time period using an instantaneous pressure drop at a time in the time period, the first pressure drop, the second pressure drop, the first water cut value, and the second water cut value.

In some embodiments, the time period includes at least one move between the first position and the second position. In some embodiments, the method includes determining an average water cut value for the downhole fluid by integrating the instantaneous water cut value over the time period. In some embodiments, the time period includes a plurality of moves between the first position and the second position. In some embodiments, the method includes determining a density of the downhole fluid from the average water cut, a density of water, and a density of oil. In some embodiments, the method includes using a pressure sensor upstream of the pressure drop device to measure an annulus pressure. In some embodiments, the method includes using a pressure sensor downstream of the pressure drop device to measure a tubing pressure. In some embodiments, the method includes determining a volumetric flow rate of the downhole fluid from a density of the downhole fluid, the annulus pressure, the tubing pressure, and a flow coefficient associated with the pressure drop device. In some embodiments, the pressure drop device includes a fluid chamber and the moveable device includes a floating member disposed in the fluid chamber, such the floating device is responsive to the density of the downhole fluid in the fluid chamber and moves the inflow device between the first position and the second position.

In another embodiment, a non-transitory computer-readable medium having executable code stored thereon is provided. The executable code having instructions that, when executed by a processor, cause the processor to perform operations that include monitoring flow of a downhole fluid through a pressure drop device, in combination with a moveable device configured to move between a first position and a second position. The first position is responsive to a first water cut for a downhole fluid and the second position is responsive to a second water cut for the downhole fluid, where the first water cut is greater than the second water cut. The operations also include determining a first pressure drop across the pressure drop device associated with the first position and determining a second pressure drop across the pressure drop device associated with the second position. The operations further include determining an instantaneous water cut value in a time period using an instantaneous pressure drop at a time in the time period, the first pressure drop, the second pressure drop, the first water cut value, and the second water cut value.

In some embodiments, the time period includes at least one move between the first position and the second position.

In some embodiments, the operations include determining an average water cut value for the downhole fluid by integrating the instantaneous water cut value over the time period. In some embodiments, the operations include determining a density of the downhole fluid from the average water cut, a density of water, and a density of oil. In some embodiments, the operations include determining an instantaneous volumetric flow rate of the downhole fluid and at the first position from a flow coefficient associated with the first position, the first pressure drop, and the first water cut. In some embodiments, the operations include determining an instantaneous fluid volumetric flow rate of the downhole fluid and at the second position from a flow coefficient associated with the second position, the second pressure drop, and the second water cut. In some embodiments, the operations include determining an average fluid volumetric flow rate over the time period by integrating an instantaneous fluid volumetric flow rate over the time period, the time period including at least one move between the first position and the second position. In some embodiments, the operations include receiving an annulus pressure from a pressure sensor upstream of the pressure drop device. In some embodiments, the operations include receiving a tubing pressure from a pressure sensor downstream of the pressure drop device. In some embodiments, the operations include determining a volumetric flow rate of the downhole fluid from a density of the downhole fluid, the annulus pressure, the tubing pressure, and a flow coefficient associated with the pressure drop device.

In another embodiment, a method of determining properties of a downhole fluid in a well is provided. The method includes monitoring, over a time period, flow of a downhole fluid through a pressure drop device disposed in the well, in combination with a moveable device configured to move between a first position and a second position. The first position is responsive to a first water cut for the downhole fluid and associated with a first pressure drop across the pressure drop device, and the second position is responsive to a second water cut for the downhole fluid and associated with a second pressure drop across the device. The method also includes determining a density of the downhole fluid using an average water cut over the time period, a density of water, and a density of oil, such that the average water cut is determined from an instantaneous water cut integrated over the time period. The method further includes determining a volumetric flow rate of the downhole fluid using the density of the downhole fluid, an annulus pressure, a tubing pressure, and a flow coefficient associated with the pressure drop device.

In some embodiments, the pressure drop device includes a fluid chamber and the moveable device includes a floating member disposed in the fluid chamber, such the floating device is responsive to the density of the downhole fluid in the fluid chamber and moves the inflow device between the first position and the second position. In some embodiments, the method includes obtaining the annulus pressure from a pressure sensor upstream of the pressure drop device. In some embodiments, the method includes obtaining the annulus pressure from a pressure sensor downstream of the pressure drop device to measure a tubing pressure. In some embodiments, the method includes determining the instantaneous water cut in the time period using an instantaneous pressure drop at a time in the time period, the first pressure drop, the second pressure drop, the first water cut value, and the second water cut value. In some embodiments, the time period includes a plurality of moves between the first position and the second position.

DETAILED DESCRIPTION

The present disclosure will be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Figure 1:
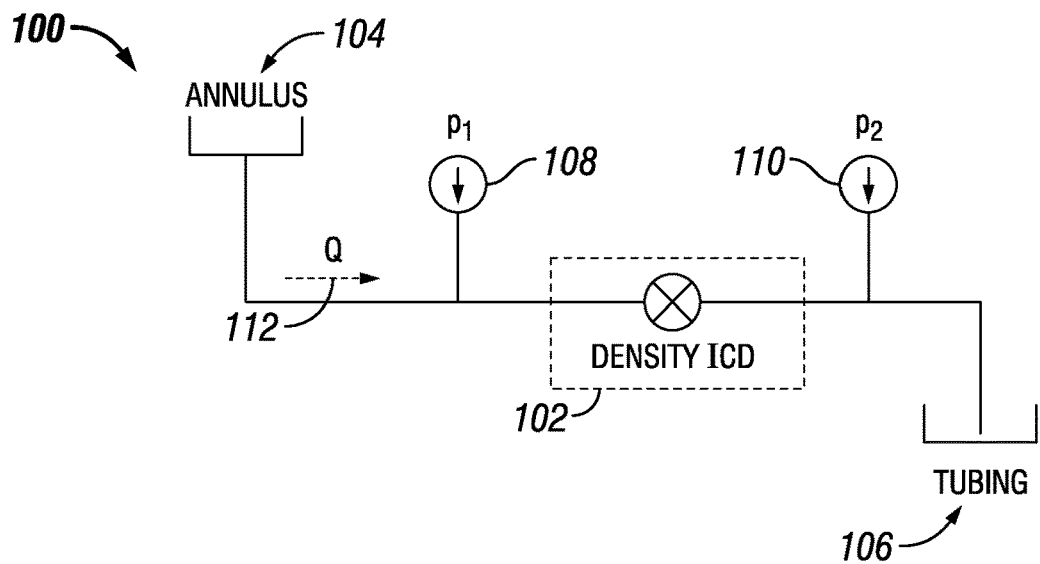
FIG. 1 is a schematic diagram of a system for determining water cut and volumetric flow rate of a downhole fluid flowing through an inflow control device in accordance with an embodiment of the disclosure.

FIG. 1 is a schematic diagram of a system for determining water cut and volumetric flow rate of a downhole fluid flowing through a pressure drop device (for example, an inflow control device) in accordance with embodiments of the disclosure. FIG. 1 depicts a section 100 of a well having a density inflow control device 102 (ICD) disposed in a wellbore between an annulus 104 and tubing 106. A first pressure sensor 108 is disposed in an upstream side of the density ICD 102 and a second pressure sensor 110 is disposed on a second downstream side of the density ICD 102. The flow of fluids from the annulus and having a volumetric flow rate Q is illustrated by arrow 112 in FIG. 1. The well section 100 may be completed using known completion techniques. The well section 100 may include any form of a hole formed in a geologic formation, such as for the purpose of locating and extracting hydrocarbons or other resources from a formation having the hydrocarbon reservoir.

As known in the art, an inflow control device may be used to equalize reservoir inflow along the wellbore of the well section 100. Although FIG. 1 depicts a well section 100 having a single ICD 102, it should be appreciated that multiple ICDs may be used in a section of well or in multiple sections of a well. As described in the disclosure, the term "density inflow control device" refers to an inflow control device that is responsive to the density of the fluid flowing through the device. Thus, as described in the disclosure, the density ICD 102 has the capability to choke flow depending on the density (as a function of the composition of water and oil) of the fluid flowing from the annulus 104.

As will be appreciated, fluid may flow from the reservoir through the annulus 104, through the density ICD 102, and into the tubing 106. The density ICD 102 may control entry of the fluid into the tubing 106 via the mechanism described in the disclosure. The first pressure sensor 108 may provide continuous annulus pressure ($p_1$) measurements and may provide reservoir pressure measurements when the well is shut-in (that is, not producing fluids). The second pressure sensor 110 may provide tubing pressure ($p_2$) measurements.

The pressure sensors 108 and 110 may be any pressure sensor suitable for use downhole in a well and may include pressure transducers or other known devices. In some embodiments, each of the pressure sensors 108 and 110 may include or be a part of an apparatus that include the capability of wireless or wired transmission pressure measurements. For example, in such embodiment the pressure sensors 108 and 110 may be coupled to an electrical conductor extending to another section of the well or to the surface. The pressure sensors 108 and 110 may be configured to periodically or continually transmit pressure measurements to another section of the well or to the surface.

Figure 2:
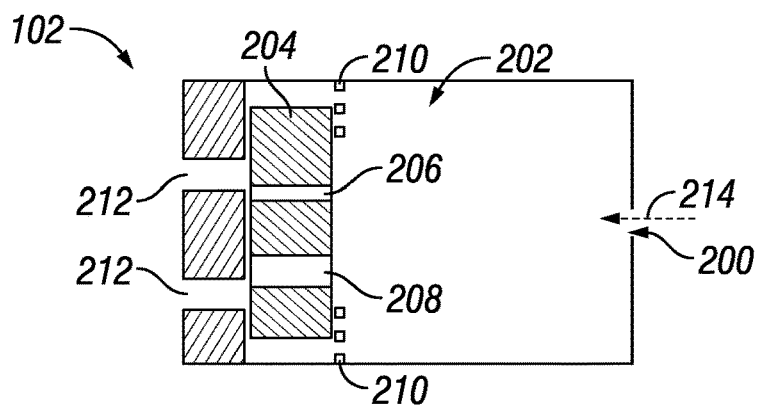
FIGS. 2-4 are schematic diagrams illustrating operation of the density inflow control device in accordance with an embodiment of the disclosure.
Figure 3:
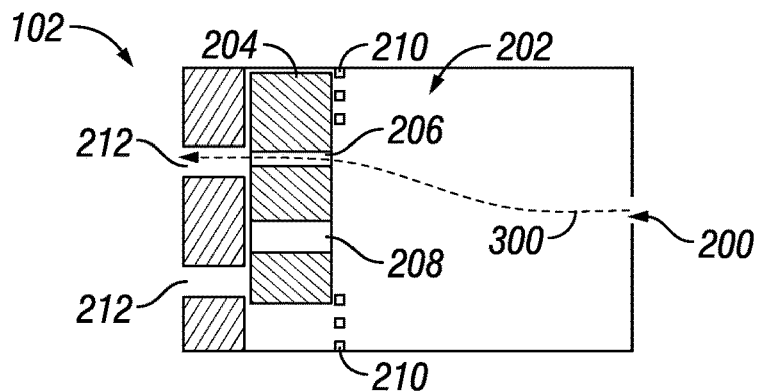
Figure 4:
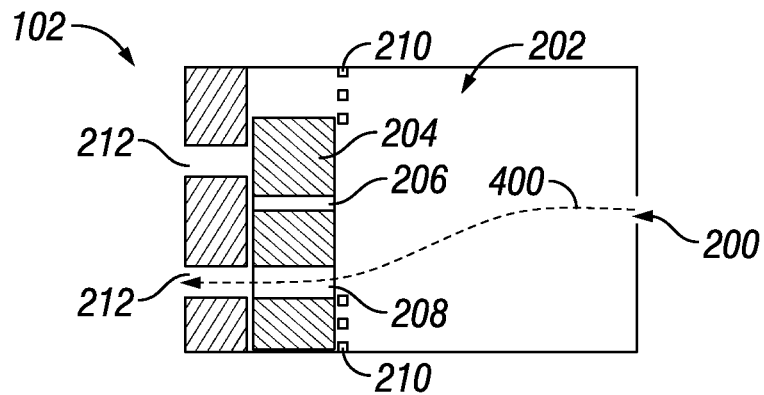

FIGS. 2-4 are schematic diagrams illustrating operation of the density ICD 102 in accordance with embodiments of the disclosure. As shown in FIGS. 2-4, the density ICD 102 may include an inlet 200, a flow chamber 202, a moveable device (for example, floating device 204 having a small orifice 206 and a large orifice 208), floating device guides 210, and outlets 212. As shown by arrow 214, fluid enters the flow chamber 202 via the inlet 200. The flow chamber 202 may enable the fluid to settle and provide laminar fluid flow through the density ICD 102. In some embodiments, the floating device guides 210 may extend from the opposed inner surfaces (for example, the "top" and "bottom") of the flow chamber 202 to assist in maintaining the floating device 204 against the outlets 212. In some embodiments, the floating device guides 210 may have opening to maintain fluid communication between the flow chamber 202 and the areas above and below the floating device 204.

The floating device 204 may have a density lower than water (that is, is lighter than water) and moves between an upper position shown in FIG. 3 and a lower position shown in FIG. 4. As shown in FIG. 3, when the density ICD 102 is flowing water (that is, when the fluid flowing through the density ICD 102 is water), the floating device 204 is in the upper position and the small orifice 206 enables restricted flow through the density ICD 102 and the large orifice 208 is blocked. The fluid flow through the ICD 102 when the floating device 204 is in the upper position is shown by arrow 300 in FIG. 3. The upper position shown in FIG. 3 may be referred to as a "restricted choke position." Conversely, as shown in FIG. 4, when the density ICD 102 is flowing oil (that is, when the fluid flowing through the density ICD 102 is oil), the floating device 204 sinks to the lower position and the large orifice 208 enables greater flow through the density ICD 102 as compared to the flow enabled by the small orifice 206 when the floating device 204 is in the upper position. The fluid flow through the ICD 102 when the floating device 204 is in the upper position is shown by arrow 400 in FIG. 4. The lower position shown in FIG. 4 may be referred to as a "relaxed choke position."

During operation (for example, during a production of fluids from a well), the amount of water in the oil flowing from the well may gradually increase. As the well begins to progressively produce more water, the flow chamber 202 of the density ICD 102 gradually fills with water. When percentage of water is great enough such that the density of the fluid in the fluid chamber 202 is greater than the density of the floating device 204, buoyancy forces cause the floating device 204 to move upwards. Conversely, once the percentage of water decreases and becomes low enough such that the density of the fluid in the fluid chamber 202 is less than the effective density of the floating device 204, the floating device 204 moves downwards. As will be appreciated, the orifices 206 and 208 are aligned such that fluid flow cannot be blocked at any point during movement of the floating device 202 (that is, at any point along the movement path of the floating device 202 one of the orifices 206 and 208 enables fluid flow through the outlets 212.

Figure 5:
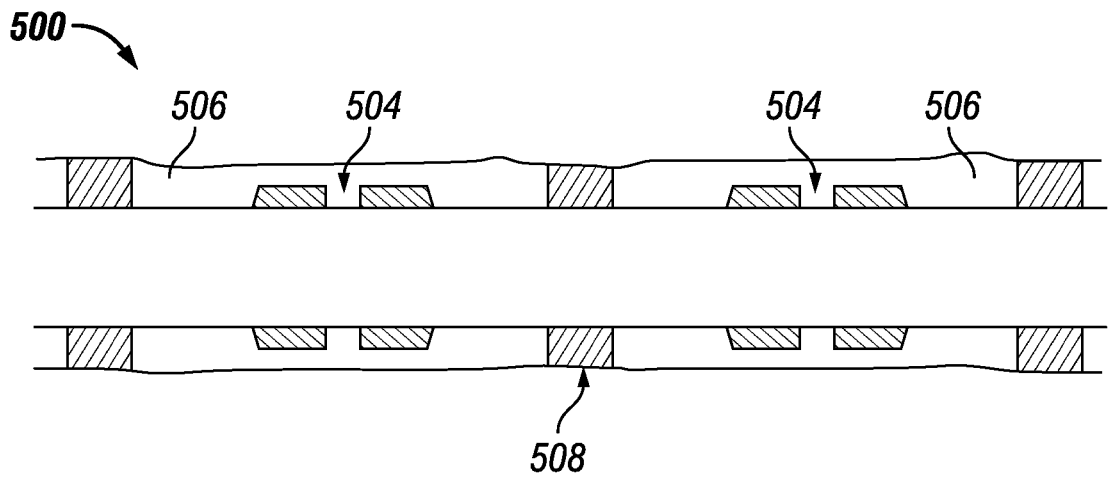
FIG. 5 is a schematic diagram of a horizontal well having density inflow control valves and compartments separated by swell packers in accordance with an embodiment of the disclosure.

Density ICDs, such as those shown in FIGS. 1-4 and discussed supra, may be used to reduce long-term water production in compartmentalized horizontal wells. In some horizontal wells, particular those horizontal wells having relatively large lengths, the production interval in the well may be separated by swell packers. FIG. 5 is a schematic diagram of horizontal well 500 with density ICDs 504 and having compartments 506 separated by swell packers 508 in accordance with an embodiment of the disclosure. As shown in FIG. 5, a density ICD may be installed in each segment to equalize the flow in the well. When a particular compartment 506 begins to produce water, the density ICD in that compartment may choke the fluid flow to reduce total production from that compartment and enable more oil to flow from other compartments, thus effectively reducing the total water content (that is, water cut) of the produced fluid from the well.

In view of the operation of a density ICD as described supra, embodiments of the disclosure may enable the determination of flow rate and water cut from a density ICD without the use of a venturi meter or other devices that directly measure flow rate or other parameters. As used in the disclosure, the term "toggling" refers to movement of the floating component of a density ICD between a position having the large orifice open to an outlet (the "relaxed choke position") and a position having the small orifice open to an outlet (the "restricted choke position"). A determination of flow rate and water cut discussed supra may rely on the following assumptions regarding the toggling of a density ICD as reservoir fluids flow through the fluid chamber.

In some embodiments, the flow chamber of a density ICD may be sized to have laminar flow at flow rates in the range of 100 barrels of fluid per day (BFD)/compartment to 300 BFD/compartment. In such embodiments, slug and stratified fluid flow may occur in the density ICD. For example, heavier fluid may accumulate in the bottom of the flow chamber and slugs of water may be periodically produced out of the flow chamber.

After a time period of fluid flow, the total density of the fluid in the flow chamber exceeds the density of the floating device (that is, the fluid in the flow chamber increases in water cut), moving the floating device upwards to a restricted choke position.

When the floating device changes position ("toggles"), water is produced out of the flow chamber and the total density of the fluid in the flow chamber begins to decrease, eventually becoming lower than the density of the floating device. As a result, the floating device moves downward (sinks) to a relaxed choke position.

A force is exerted on the floater when it is pushed by the fluid against the wall of the outlets, causing friction between the floating device and the outlets wall as the floating devices changes position and moves up and down. As a result, the density (expressed in terms of water cut $WC_{up}$) at which the floating device moves upward is different than the density (expressed as water cut at which the floating device moves downward (expressed in terms of $WC_{down}$). The values of $WC_{up}$ and $WC_{down}$ may be controlled by adjusting the surface roughness of the floating device and the outlets wall of the density ICD.

Figure 6:
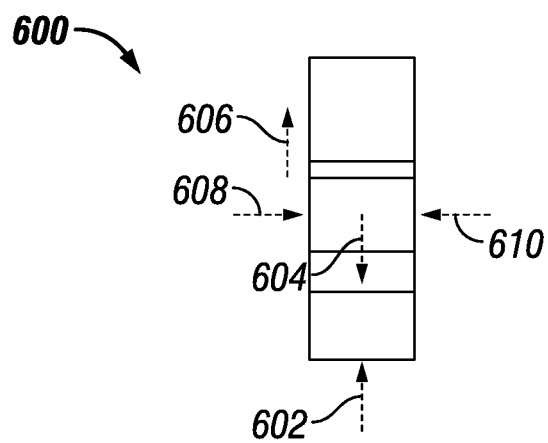
FIG. 6 is a schematic diagram of the forces acting on a floating device of a density inflow control valve in accordance with an embodiment of the disclosure.

FIG. 6 is a schematic diagram of the forces acting on a moveable device (for example, a floating device 600) of a density ICD in accordance with an embodiment of the disclosure. The forces shown in FIG. 6 include a buoyancy force $F_B$ (shown by arrow 602), the weight of the floater $F_w$ (shown by arrow 604), the friction force $F_{fr}$ (shown by arrow 606, although as will be appreciated the friction force acts against the direction of movement of the floating device 600), the normal force $F_N$ (shown by arrow 608), and the force of the fluid in the flow chamber, $F_{fluid}$ (shown by arrow 610). The vertical force balance ($\Sigma F$) acting on the floating device 600 for the restricted choke position may be represented by Equation 1:

$$\Sigma F = F_B - F_W - F_{fr} = Vg(\rho_{fluid} - \rho_{float}) - F_{fr} \quad (1)$$

Where $F_B$ is the buoyancy force, $F_w$, is the weight of the floater, $F_{fr}$ is the friction force, V is the volume of the floater, g is the gravitational acceleration, $\rho_{fluid}$ is the density of the fluid, and $\rho_{float}$ is the density of the floating device.

The vertical force balance acting on the floating device 600 for the relaxed choke position may be represented by Equation 2:

$$\Sigma F = F_B - F_W + F_{fr} = Vg(\rho_{fluid} - \rho_{float}) - F_{fr} \quad (2)$$

Each time a density ICD toggles between positions, the area open to fluid flow changes. As a result, the pressure across the density ICD will change according to Equation 3:

$$\Delta p_{ICD} = p_1 - p_2 \quad (3)$$

Where $\Delta p_{ICD}$ is the change in pressure, $p_1$ is the pressure across the density ICD when the floating device is a first position, and $p_2$ is the pressure across the density ICD when the floating device is in a second position.

Figure 7:
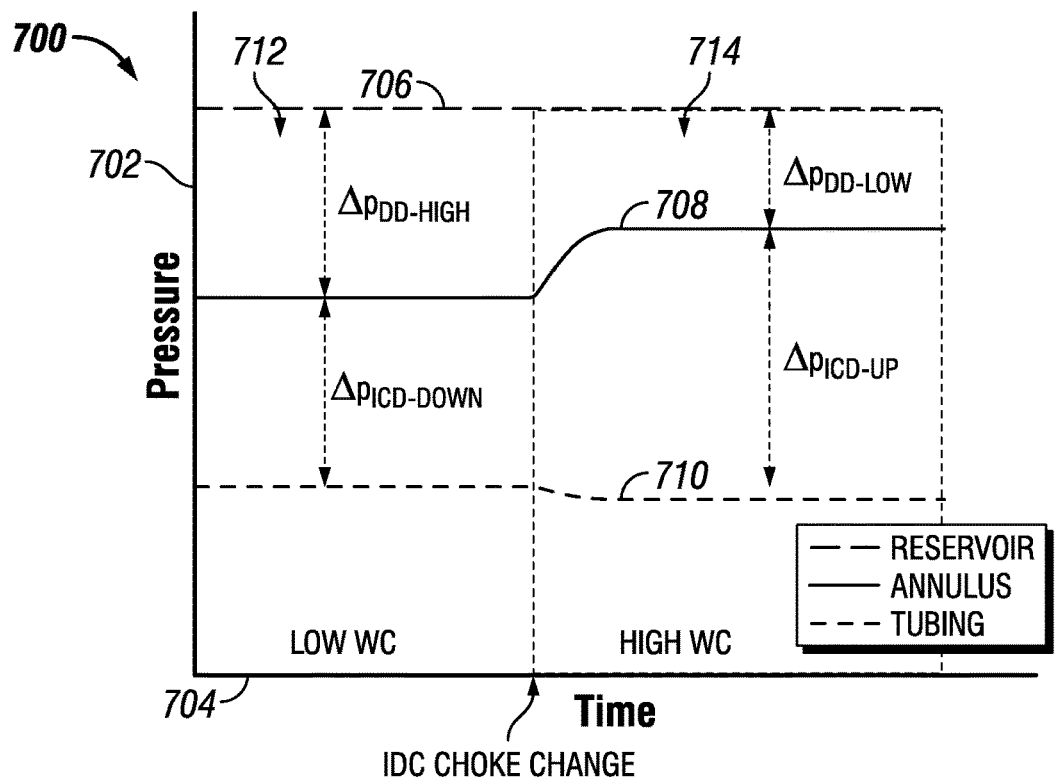
FIG. 7 is a plot of pressure versus (vs.) time depicting reservoir pressure, annulus pressure, and tubing pressure over a time period that includes toggling of a density inflow control device in accordance with an embodiment of the disclosure.

While the density ICD toggles from the relaxed choke position to the restricted choke position, the reservoir pressure is unchanged and the tubing pressure drops slightly due to the decreased flow rate through the density ICD, reducing the frictional losses in that section. FIG. 7 is a plot 700 of pressure vs. time illustrating the trends of the reservoir, annulus, and tubing pressures during toggling of the density ICD in accordance with an embodiment of the disclosure. As shown in FIG. 7, the y-axis 702 depicts pressure and the x-axis 704 depicts time. Line 706 depicts reservoir pressure, line 708 depicts annulus pressure, and line 710 depicts tubing pressure. The plot 700 depicts a first region 712 corresponding to a lesser water cut in the fluid flowing through the density ICD and a second region 714 corresponding to a greater water cut (that is, after the density ICD toggles). As shown by line 706, the reservoir pressure is unchanged. As shown by line 708, the annulus pressure increases after the density ICD toggles, while as shown by line 710, the tubing pressure decreases. The plot 700 graphically illustrates various pressure changes. As shown in FIG. 7, $\Delta p_{DD-high}$ corresponds to the high drawdown pressure and $\Delta p_{DD-low}$ corresponds to the low drawdown pressure. As also shown in FIG. 7, $\Delta p_{ICD-down}$ corresponds to the pressure drop across the density ICD when the density ICD is in the relaxed choke position and $\Delta p_{ICP-up}$ corresponds to the pressure drop across the density ICD when the density ICD is in the relaxed choke position.

As discussed in the disclosure, the flow rate (and water cut) of the fluid flowing through the density ICD may be determined by monitoring the change of the pressure across the density ICD as the ICD toggles back and forth between the relaxed choke position and the restricted choke position.

Figure 8:
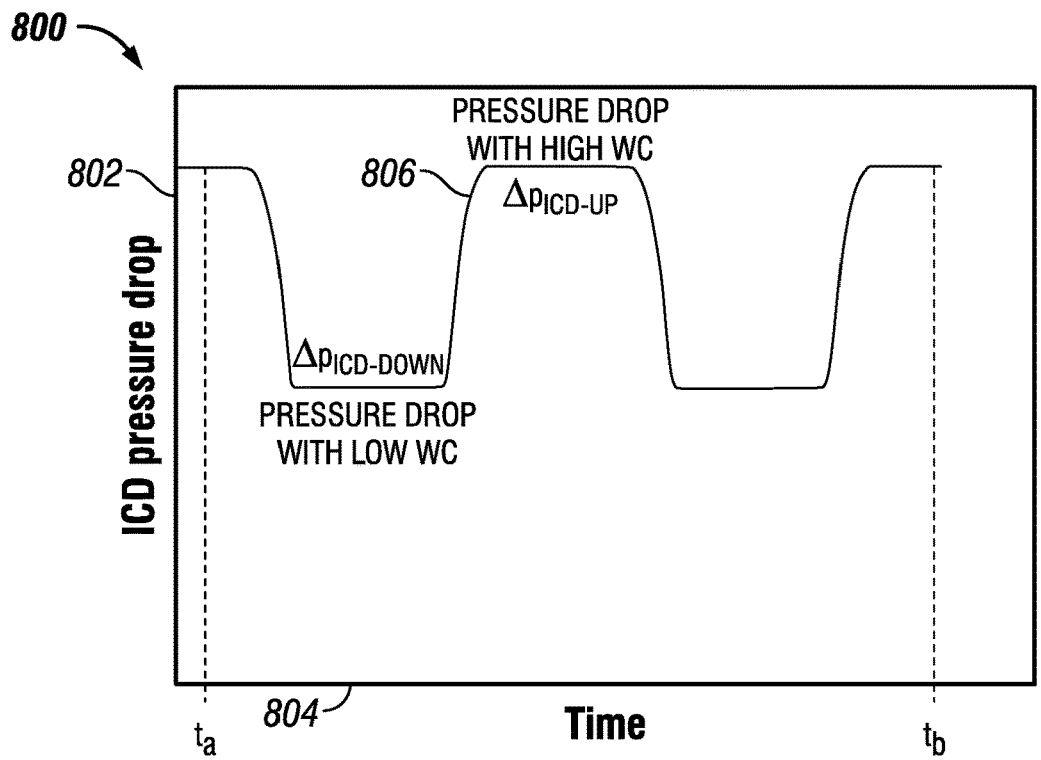
FIG. 8 is a plot of a pressure drop across a density inflow control device vs. time in accordance with an embodiment of the disclosure.

In certain embodiments, pressure sensors located before and after the density ICD may provide monitoring of the density ICD pressure drop change. For example, as shown in FIG. 1, pressure sensors 108 and 110 may provide monitoring of the pressure drop change (that is, between pressures $p_1$ and $p_2$ shown in FIG. 1) across the density ICD 102. When the fluid flow is at steady-state, $\Delta p_{ICD}$ may be plotted as a function of time. FIG. 8 depicts a plot 800 of density ICD pressure drop ($\Delta p_{ICD}$) vs. time in accordance with an embodiment of the disclosure. FIG. 8 depicts the density ICD pressure drop on the y-axis 802 and time on the x-axis 804. Line 806 shows the pressure drop for a time period from a time $t_a$ to a time $t_b$. The modulation cycles between the low water cut ($\Delta p_{ICD-down}$) and high water cut ($\Delta p_{ICD-up}$) periods from a time $t_a$ to a time $t_b$ are shown in the plot 800.

As will be appreciated, for the same surface and reservoir conditions (for example, reservoir pressure), $\Delta p_{ICD-down}$ and $\Delta p_{ICD-up}$ will be constant. If the surface and reservoir conditions (for example, reservoir pressure) change, the ICD pressure drop values may be re-identified accordingly.

In some embodiments, pressure sensors may monitor the pressure drop across the density ICD continuously and in real-time. The continuous and real-time monitoring of the pressure drop may provide for the averaging of the pressure drop over relatively greater periods of time. A determination of the volumetric flow rate and water cut according to the techniques described in the disclosure may use a selected time period having a duration long enough to experience at least one toggle between the positions of a density ICD. Upon selection of a time period, the instantaneous water cut at a time t may be determined according to Equation 4:

$$WC(t) = \left[\frac{\Delta p(t) - \Delta p_{ICD-down}}{\Delta p(t) - \Delta p_{ICD-up}}\right][WC_{up} - WC_{down}] + WC_{down} \quad (4)$$

Where WC(t) is the instantaneous water cut, $WC_{up}$ is the water cut value at which the floating device in the density ICD moves upward to the restricted choke position, $WC_{down}$ is the water cut value at which the floating device in the density ICD moves downward to the relaxed choke position, $\Delta p(t)$ is the instantaneous pressure drop across the density ICD, $\Delta p_{ICD-up}$ is the pressure drop across the density ICD when the ICD is the in the upper position (restricted choke position) and $\Delta p_{ICD-down}$ is the pressure drop across the density ICD when the ICD is the in the lower position (relaxed choke position).

The average water cut ($WC_{avg}$) over a selected time period may be determined by integrating the area under the instantaneous water cut plot (for example, for the period starting at time $t_a$ and ending at time $t_b$ illustrated in FIG. 8), as shown in Equation 5:

$$WC_{avg} = \int_{t_a}^{t_b} WC(t) \cdot dt \quad (5)$$

The density of the fluid flowing through the density ICD may be determined for use in the determination of the volumetric flow rate. As will be appreciated, single-phase properties for water ($\rho_w$) and oil ($\rho_o$) at downhole conditions may be determined from pressure-volume-temperature (PVT) analysis using known techniques. Accordingly, the density ($\rho_m$) of the fluid mixture flowing through the density ICD may be determined according to Equation 6:

$$\rho_m = WC_{avg} \cdot \rho_w + (1 - WC_{avg}) \rho_o \qquad (6)$$

Once the mixture density is determined, the volumetric flow rate thorough the density ICD may be determined according to Equation 7:

$$Q = C \sqrt{\frac{p_1 - p_2}{\rho_m}} \qquad (7)$$

Where $p_1$ is the annulus pressure provided by the first pressure sensor upstream of the density ICD, $p_2$ is the tubing pressure provided by the second pressure sensor downstream of the density ICD, and C is the flow coefficient of the ICD. The flow coefficient C is dependent on whether the fluid flow through the density ICD is through the small orifice (that is, the restricted choke position) or through the large orifice (that, the relaxed choke position). The flow coefficient C may be determined by matching the current pressure drop across the ICD with the expected pressure drop across the ICD, as shown by Equation 8:

$$C = \begin{cases} C_{big} & \text{if } \Delta p(t) = \Delta p_{ICD-down} \\ C_{small} & \text{if } \Delta p(t) = \Delta p_{ICD-up} \end{cases} \qquad (8)$$

Where $C_{big}$ is the flow coefficient of the large orifice and $C_{small}$ is the flow coefficient of the small orifice. As will be appreciated, for a particular density ICD, the flow coefficient may be determined experimentally or provided by a manufacturer. In other embodiments, the flow coefficient C may be determined using a venturi meter positioned upstream of the inlet to a pressure drop device (for example, an inflow control device) or downstream of the outlet of a pressure drop device (for example, an inflow control device). In such embodiments, the flow coefficient C used in Equation 7 may be determined directly from flow coefficient of the venturi meter and Δp is the pressure drop across the venturi meter.

As will be appreciated, in other embodiments, an instantaneous volumetric flow rate at the restricted choke position may be determined from a flow coefficient associated with an ICD when the ICD is in the restricted choke position, a pressure drop across the ICD in the restricted choke position, and the water cut associated with the restricted choke position. Similarly, an instantaneous volumetric flow rate at the relaxed choke position may be determined from a flow coefficient associated with an ICD when the ICD is in the relaxed choke position, a pressure drop across the ICD in the relaxed choke position, and the water cut associated with the relaxed choke position. In such embodiments, an instantaneous volumetric flow rate may be determined by integrating an instantaneous volumetric flow rate over a time period (that is, in a manner similar to the determination of an instantaneous water cut as described supra, such that the time period includes at least one toggle between the restricted choke position and relaxed choke position).

Figure 9:
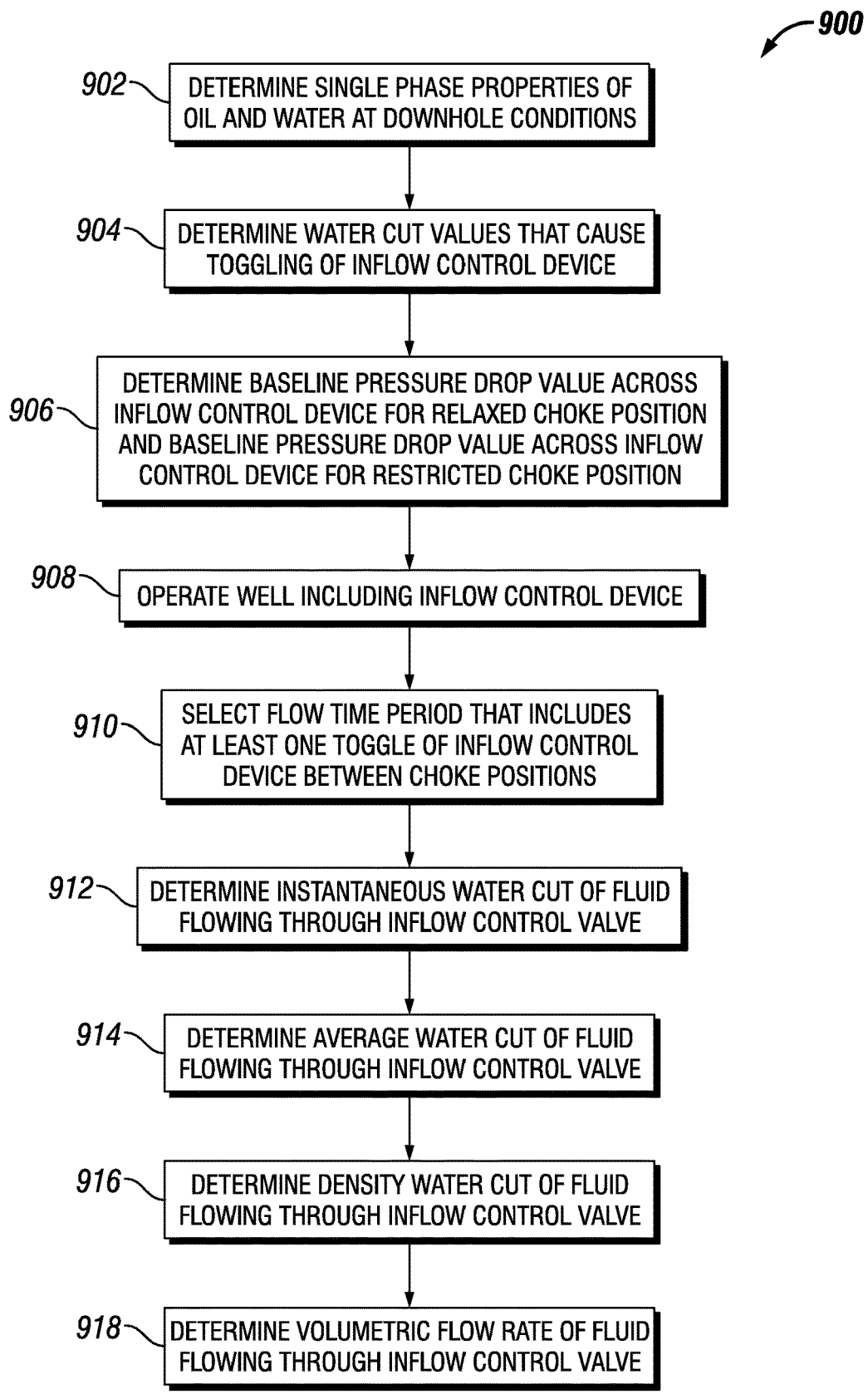
FIG. 9 is a block diagram of a process for determining a water cut and volumetric flow rate of a downhole fluid flowing through a density inflow control valve in accordance with an embodiment of the disclosure.

FIG. 9 depicts a process 900 for using a pressure drop device (for example, an inflow control device (ICD)) to determine the water cut and flow rate of a downhole fluid in accordance with an embodiment of the disclosure. Initially, the single phase properties (for example, density) of oil and water at the downhole conditions (for example, temperature and pressure) may be determined (block 902) using known techniques. For example, single phase properties for oil and water at various conditions may be available from a database of fluid properties or calculated using known properties at certain temperatures and pressures. Additionally, the water cut values that cause toggling of the inflow control device between a relaxed choke position and a restricted choke position may be determined (block 904). As will be appreciated, for a particular ICD, water cut values may be determined experimentally (for example, in a laboratory) or provided by a manufacturer.

Next, a baseline pressure drop value across the inflow control device in the relaxed choke position and a baseline pressure drop value across the inflow control device in the restricted choke position may be determined (block 906). Here again, for a particular ICD, water cut values may be determined experimentally (for example, in a laboratory) or provided by a manufacturer.

The inflow control device may then be used in the operation of a well, such as to control flow from, for example, a compartment of a horizontal well (block 908). As will be appreciated, the inflow control device may be used to restrict fluid flow from a compartment when the water cut in the fluid is greater than a certain value so that hydrocarbon production from the well is optimized. A flow time period that includes at least one toggle of the inflow control device may be selected (block 910). It should be appreciated that in some embodiments the flow time period may include multiple toggles of the inflow control device. Additionally, the current pressure drop across the inflow control device may be identified as a pressure drop associated with the restricted choke position or the relaxed choke position of the inflow control device.

Next, the instantaneous water cut value with respect to time may be determined from the instantaneous pressure drop, the pressure drop and water cut associated with the relaxed choke position, and the pressure drop and water cut associated with the restricted choke position (block 912), as described supra in Equation 4. Next, the average water cut of the fluid flowing through the inflow control device may be determined by integrating the instantaneous water cut over time (block 914), as described supra in Equation 5.

As also discussed in the disclosure, the volumetric flow rate of the fluid flowing through the inflow control device may be determined. In such embodiments, the density of the downhole fluid may first be determined from the single phase density of water, single phase density of oil, and the average water cut (block 916), as shown in Equation 6 described supra. The volumetric flow rate of the downhole fluid flowing through the inflow control device may be determined from the annulus pressure (upstream of the inflow control pressure), the tubing pressure downstream of the inflow control device), the density of the downhole fluid, and a flow coefficient associated with the inflow control device (block 918), according to Equation 7 discussed supra.

Advantageously, the water cut value and volumetric flow rate determined using the techniques described in the disclosure may be significantly faster than existing techniques and may decrease costs. For example, determining the water cut value and volumetric flow rate from downhole pressure sensors avoids the use of well intervention or production logging operations that are relatively expensive, time-consuming, and intrusive. Additionally, the water cut value and volumetric flow rate determinations described in the disclosure eliminate the use of nuclear sources and x-ray or microwave devices for measuring downhole fluids, as such sources and devices may present safety and reliability problems.

The water cut value, the volumetric flow rate, or both may be used to change production operations or components associated with a well. For example, a water cut value may indicate that a particular compartment is producing an unacceptable amount of water and the compartment may be isolated from further production. The volumetric flow rate may be used to determine the overall production rate of a well that is used in cost and profitability analysis. The water cut value, volumetric flow rate, or both may result in performance of an enhanced oil recovery (EOR) operations to increase production from the well.

In some embodiments, the pressure sensors may be coupled to a monitoring system. In such embodiments, a monitoring system located at the surface may receive signals from the pressure sensors and use the received pressure measurements to determine the water cut and volumetric flow rate in accordance with the techniques described in the disclosure. For example, a monitoring system may be coupled to the pressure sensors via one or more electrical conductors that extend from the surface into a well and enable the communication of signals between the pressure sensors and the monitoring system.

An example water cut and flow rate monitoring system may be or include a computer or computing devices. In some embodiments, for example, a monitoring system may include a processor, a memory, and a display. As will be appreciated, in some embodiments a monitoring system may include other components such as a network interface, input device, et cetera (etc).

A processor of an example monitoring system (as used in the disclosure, the term "processor" encompasses microprocessors) may include one or more processors having the capability to receive and process data from a well, such as data obtained from pressure sensors located in the well. In some embodiments, the processor may include an application-specific integrated circuit (AISC). In some embodiments, the processor may include a reduced instruction set (RISC) processor. Additionally, the processor may include a single-core processors and multicore processors and may include graphics processors. Multiple processors may be employed to provide for parallel or sequential execution of one or more of the techniques described in the disclosure. The processor may receive instructions and data from a memory (for example, memory).

The memory of an example monitoring system (which may include one or more tangible non-transitory computer readable storage mediums) may include volatile memory, such as random access memory (RAM), and non-volatile memory, such as read only memory (ROM), flash memory, a hard drive, any other suitable optical, magnetic, or solid-state storage medium, or a combination thereof. The memory may be accessible by the processor. The memory may store executable computer code. The executable computer code may include computer program instructions for implementing one or more techniques described in the disclosure. For example, the executable computer code may include water cut and volumetric flow rate determination instructions to implement one or more embodiments of the present disclosure, such as one or more steps of the process 900 described supra. In some embodiments, the water cut and volumetric flow rate determination instructions may receive as input pressure measurements over a time period from pressure sensors upstream and downstream of a pressure drop device (for example, an inflow control device, such as in the configuration shown in FIG. 1) and provide a water cut value of a downhole fluid flowing through a pressure drop device (for example, an inflow control device). Additionally, in some embodiments, the water cut and volumetric flow rate determination instructions may output a volumetric flow rate of the fluid flowing through a pressure drop device (for example, an inflow control device). The outputs may be stored in the memory of the monitoring system.

In some embodiments, an example monitoring system may include a display that provides a water cut value, volumetric flow rate, or both on the display for viewing by an operator. Such a display may include a cathode ray tube (CRT) display, liquid crystal display (LCD), an organic light emitting diode (OLED) display, or other suitable display. In some embodiments, the display may display a user interface (for example, a graphical user interface). In accordance with some embodiments, the display may be a touch screen and may include or be provided with touch sensitive elements through which a user may interact with the user interface. In some embodiments, the display may display the water cut value, volumetric flow rate, or both, of a downhole fluid determined in accordance with the techniques described in the disclosure.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A method of determining properties of a downhole fluid in a well, comprising:
   using a pressure drop device in the well, in combination with a moveable device configured to move between a first position and a second position, the first position responsive to a first water cut for a downhole fluid and the second position responsive to a second water cut for the downhole fluid, the first water cut greater than the second water cut;
   determining a first pressure drop across the pressure drop device associated with the first position;
   determining a second pressure drop across the pressure drop device associated with the second position; and
   determining an instantaneous water cut value in a time period using an instantaneous pressure drop at a time in the time period, the first pressure drop, the second pressure drop, the first water cut value, and the second water cut value.

2. The method of claim 1, wherein the time period comprises at least one move between the first position and the second position.

3. The method of claim 2, comprising determining an average water cut value for the downhole fluid by integrating the instantaneous water cut value over the time period.

4. The method of claim 3, wherein the time period comprises a plurality of moves between the first position and the second position.

5. The method of claim 3, comprising determining a density of the downhole fluid from the average water cut, a density of water, and a density of oil.

6. The method of claim 1, comprising using a pressure sensor upstream of the pressure drop device to measure an annulus pressure.

7. The method of claim 6, comprising using a pressure sensor downstream of the pressure drop device to measure a tubing pressure.

8. The method of claim 7, comprising determining a volumetric flow rate of the downhole fluid from a density of the downhole fluid, the annulus pressure, the tubing pressure, and a flow coefficient associated with the pressure drop device.

9. The method of claim 1, wherein the pressure drop device comprises a fluid chamber and the moveable device comprises a floating member disposed in the fluid chamber, such that the floating device is responsive to the density of the downhole fluid in the fluid chamber and moves the moveable device between the first position and the second position.

10. A non-transitory computer-readable medium having executable code stored thereon, the executable code comprising instructions that, when executed by a processor, cause the processor to perform the following operations:
monitoring flow of a downhole fluid through a pressure drop device, in combination with a moveable device configured to move between a first position and a second position, the first position responsive to a first water cut for a downhole fluid and the second position responsive to a second water cut for the downhole fluid, the first water cut greater than the second water cut;
determining a first pressure drop across the pressure drop device associated with the first position;
determining a second pressure drop across the pressure drop device associated with the second position; and
determining an instantaneous water cut value in a time period using an instantaneous pressure drop at a time in the time period, the first pressure drop, the second pressure drop, the first water cut value, and the second water cut value.

11. The non-transitory computer-readable medium of claim 10, wherein the time period comprises at least one move between the first position and the second position.

12. The non-transitory computer-readable medium of claim 10, the operations comprising determining an average water cut value for the downhole fluid by integrating the instantaneous water cut value over the time period.

13. The non-transitory computer-readable medium of claim 12, the operations comprising determining a density of the downhole fluid from the average water cut value, a density of water, and a density of oil.

14. The non-transitory computer-readable medium of claim 10, the operations comprising determining an instantaneous volumetric flow rate of the downhole fluid at the first position from a flow coefficient associated with the first position, the first pressure drop, and the first water cut.

15. The non-transitory computer-readable medium of claim 10, the operations comprising determining an instantaneous fluid volumetric flow rate of the downhole fluid at the second position from a flow coefficient associated with the second position, the second pressure drop, and the second water cut.

16. The non-transitory computer-readable medium of claim 10, comprising determining an average fluid volumetric flow rate over the time period by integrating an instantaneous fluid volumetric flow rate over the time period, the time period including at least one move between the first position and the second position.

17. The non-transitory computer-readable medium of claim 10, comprising receiving an annulus pressure from a pressure sensor upstream of the pressure drop device.

18. The non-transitory computer-readable medium of claim 17, comprising receiving a tubing pressure from a pressure sensor downstream of the pressure drop device.

19. The non-transitory computer-readable medium of claim 18, the operations comprising determining a volumetric flow rate of the downhole fluid from a density of the downhole fluid, the annulus pressure, the tubing pressure, and a flow coefficient associated with the pressure drop device.

20. A method of determining properties of a downhole fluid in a well, comprising:
monitoring, over a time period, flow of a downhole fluid through a pressure drop device disposed in the well, in combination with a moveable device configured to move between a first position and a second position, the first position responsive to a first water cut for the downhole fluid and associated with a first pressure drop across the pressure drop device, and the second position responsive to a second water cut for the downhole fluid and associated with a second pressure drop across the pressure drop device;
determining a density of the downhole fluid from an average water cut over the time period, a density of water, and a density of oil, the average water cut determined from an instantaneous water cut integrated over the time period; and
determining a volumetric flow rate of the downhole fluid from the density of the downhole fluid, an annulus pressure, a tubing pressure, and a flow coefficient associated with the pressure drop device.

21. The method of claim 20, wherein the pressure drop device comprises a fluid chamber and the moveable device comprises a floating member disposed in the fluid chamber, such that the floating device is responsive to the density of the downhole fluid in the fluid chamber and moves the moveable device between the first position and the second position.

22. The method of claim 20, comprising obtaining the annulus pressure from a pressure sensor upstream of the pressure drop device.

23. The method of claim 20, comprising obtaining the tubing pressure from a pressure sensor downstream of the pressure drop device.

24. The method of claim 20, comprising determining the instantaneous water cut in the time period using an instantaneous pressure drop at a time in the time period, the first pressure drop, the second pressure drop, the first water cut value, and the second water cut value.

25. The method of claim 20, wherein the time period comprises a plurality of moves between the first position and the second position.

\* \* \* \* \*